United States Patent
Schillig

(10) Patent No.: US 12,357,484 B2
(45) Date of Patent: Jul. 15, 2025

(54) HINGE BRACE

(71) Applicant: Jeremiah Schillig, Mansfield, TX (US)

(72) Inventor: Jeremiah Schillig, Mansfield, TX (US)

( * ) Notice: Subject to any disclaimer, the term of this patent is extended or adjusted under 35 U.S.C. 154(b) by 491 days.

(21) Appl. No.: 17/709,570

(22) Filed: Mar. 31, 2022

(65) Prior Publication Data

US 2023/0310193 A1    Oct. 5, 2023

(51) Int. Cl.
*A61F 5/01*    (2006.01)

(52) U.S. Cl.
CPC .......... *A61F 5/0102* (2013.01); *A61F 5/0123* (2013.01); *A61F 2005/0139* (2013.01); *A61F 2005/0158* (2013.01); *A61F 2005/0165* (2013.01); *A61F 2005/0167* (2013.01)

(58) Field of Classification Search
CPC ............ A61F 5/0102; A61F 2005/0139; A61F 2005/0158; A61F 2005/0165; A61F 5/01; A61F 5/37; A61H 2201/1642; A61H 2201/165; A61H 3/00; A61H 1/024; E05D 3/06; E05D 3/122
USPC ................ 602/16, 23, 26; 16/354, 366, 371
See application file for complete search history.

(56) References Cited

U.S. PATENT DOCUMENTS

| | | | | |
|---|---|---|---|---|
| 4,384,744 A | * | 5/1983 | Barley | B60N 2/236 297/367 R |
| 2011/0071450 A1 | * | 3/2011 | Chiang | A61F 5/0123 602/16 |
| 2014/0308065 A1 | * | 10/2014 | DeHarde | F16F 1/10 403/113 |
| 2015/0223958 A1 | * | 8/2015 | Dunn | A61F 5/0102 602/16 |
| 2019/0167461 A1 | * | 6/2019 | Turconi | A61F 5/0102 |

OTHER PUBLICATIONS

ACTEK 5,000 LBS Swivel Hoist Ring (Year: 2018).*

* cited by examiner

*Primary Examiner* — Keri J Nelson
*Assistant Examiner* — Seth R. Brown
(74) *Attorney, Agent, or Firm* — Norred Law, PLLC

(57) ABSTRACT

A hinge brace system including a first upright, a second upright, a gear, a cam, and a pin associated with each of the first upright and second upright, and a dial assembly opposite the gear housing. The dial assembly includes a dial base and a dial flange, the dial flange configured to rotatably step the cam, causing the gear to step about the gear housing. The gear further includes a limit marking, the limit marking extruding from the gear into a slot of the upright and preventing the upright from travelling beyond a desired angle, the angle preventing rotation of the hinge brace system in at least one of extension and flexion.

14 Claims, 24 Drawing Sheets

600

1000

1300

1500

HINGE BRACE

FIELD OF THE INVENTION

The present invention relates to brace systems and, more specifically, to hinge brace systems having flexion and extension limits.

BACKGROUND

In spite of our efforts, injuries are a reality of life. Managing recovery from those injuries can impact our quality of life as well as the body's ability to sufficiently heal from the injury. One group of mechanisms for managing injuries are braces, specifically range of motion braces that utilize hinges that can immobilize the joint or allow partial, or sometimes full, ranges of motion while using the brace. Braces are typically used to protect an anatomical joint from unwanted flexion and extension during recovery from the injury.

There are three primary categories of hinged braces: post-operation style braces, pin style braces, and stop style braces. Post-operation style braces can be bulky and difficult to maneuver in causing issues for smaller patients or on smaller anatomical joints. Pin style braces can be more complicated to adjust and inherently contain a risk of losing the pin and rendering the brace ineffective. Stop style braces typically must be removed from the patient to be adjusted and can be complicated and/or time consuming in operation. A disadvantage of each of these types of braces is the large angular changes between positions, typically incrementing in 10-20 degree changes or greater.

SUMMARY OF THE INVENTION

The present invention includes a hinge brace system including a first upright including gear teeth on an end internal to a joint of the hinge brace system, a second upright including gear teeth on an end internal to the joint of the hinge brace system, the gear teeth of the second upright meshed with the gear teeth of the first upright, a gear, a cam, and a pin associated with each of the first upright and second upright, and a dial assembly opposite the gear housing. The gears include an internal cavity configured to receive the cams and the cams include another internal cavity configured to receive the pins. The gear, cam, and pin are internal to a gear housing. The dial assembly includes a dial base and a dial flange, the dial flange configured to rotatably step the cam, causing the cam to step the gear about the gear housing. The gear further includes a limit marking, the limit marking extruding from the gear into a slot of the upright and preventing the upright from travelling beyond a desired angle, the angle preventing rotation of the hinge brace system in at least one of extension and flexion.

DETAILED DESCRIPTION OF THE INVENTION

The terminology used herein is for the purpose of describing particular embodiments only and is not intended to be limiting of the invention. As used herein, the term "and/or" includes any and all combinations of one or more of the associated listed items. As used herein, the singular forms "a", "an", and "the" are intended to include the plural forms as well as the singular forms, unless the context clearly indicates otherwise. It will be further understood that the terms "comprises" and "comprising", when used in this specification, specify the presence of stated features, steps, operations, elements, and components, but do not preclude the presence or addition of one or more other features, steps, operations, elements, components, or groups thereof.

Unless otherwise defined, all terms (including technical and scientific terms) used herein have the same meaning as commonly understood by one having ordinary skill in the art to which this invention belongs. It will be further understood that terms, such as those defined in commonly used dictionaries, should be interpreted as having a meaning that is consistent with their meaning in the context of the relevant art and the present disclosure and will not be interpreted in an idealized or overly formal sense unless expressly so defined herein.

In describing the invention, it will be understood that a number of techniques and steps are disclosed. Each of these has individual benefit and each can also be used in conjunction with one or more, or in some cases all, of the other disclosed techniques. Accordingly, for the sake of clarity, this description will refrain from repeating every possible combination of the individual steps in an unnecessary fashion. Nevertheless, the specification and claims should be read with the understanding that such combinations are entirely within the scope of the invention and the claims.

The present disclosure is to be considered as an exemplification of the invention, and is not intended to limit the invention to the specific embodiments illustrated by the figures or description below.

Figure 1:
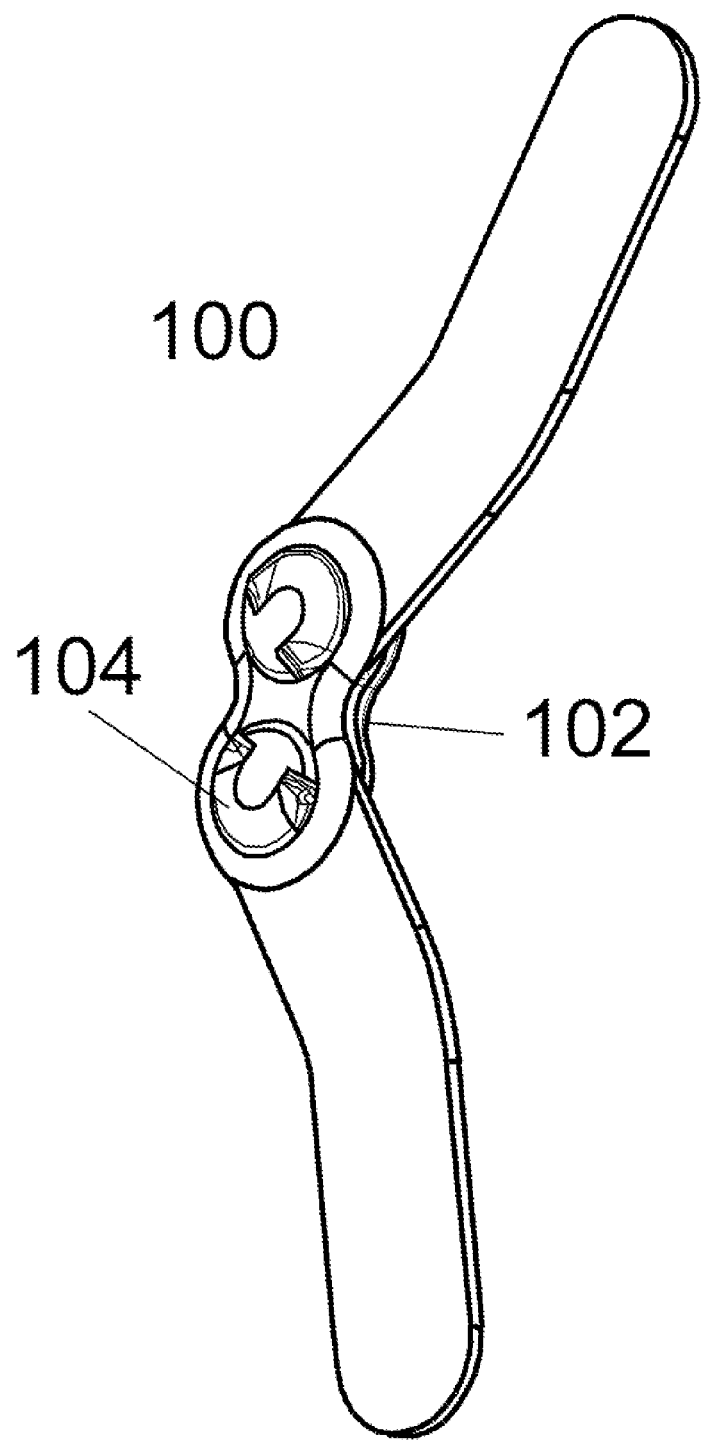
FIG. 1 is a front perspective of a hinge brace system.

The present invention will now be described by referencing the appended figures representing preferred embodiments. FIG. 1 depicts a front perspective of a hinge brace system 100. The hinge brace system 100 may comprise a joint 102 comprised of at least one dial 104. The joint 102, also referred to as a hinge, may be a flexion and extension joint that may be locked at a plurality of angles.

The hinge brace system 100 may be configured to be small relative to other brace systems. In one embodiment, the joint 102 may comprise an adjustment mechanism such as, but not limited to, a cycloidal gear.

Figure 2:
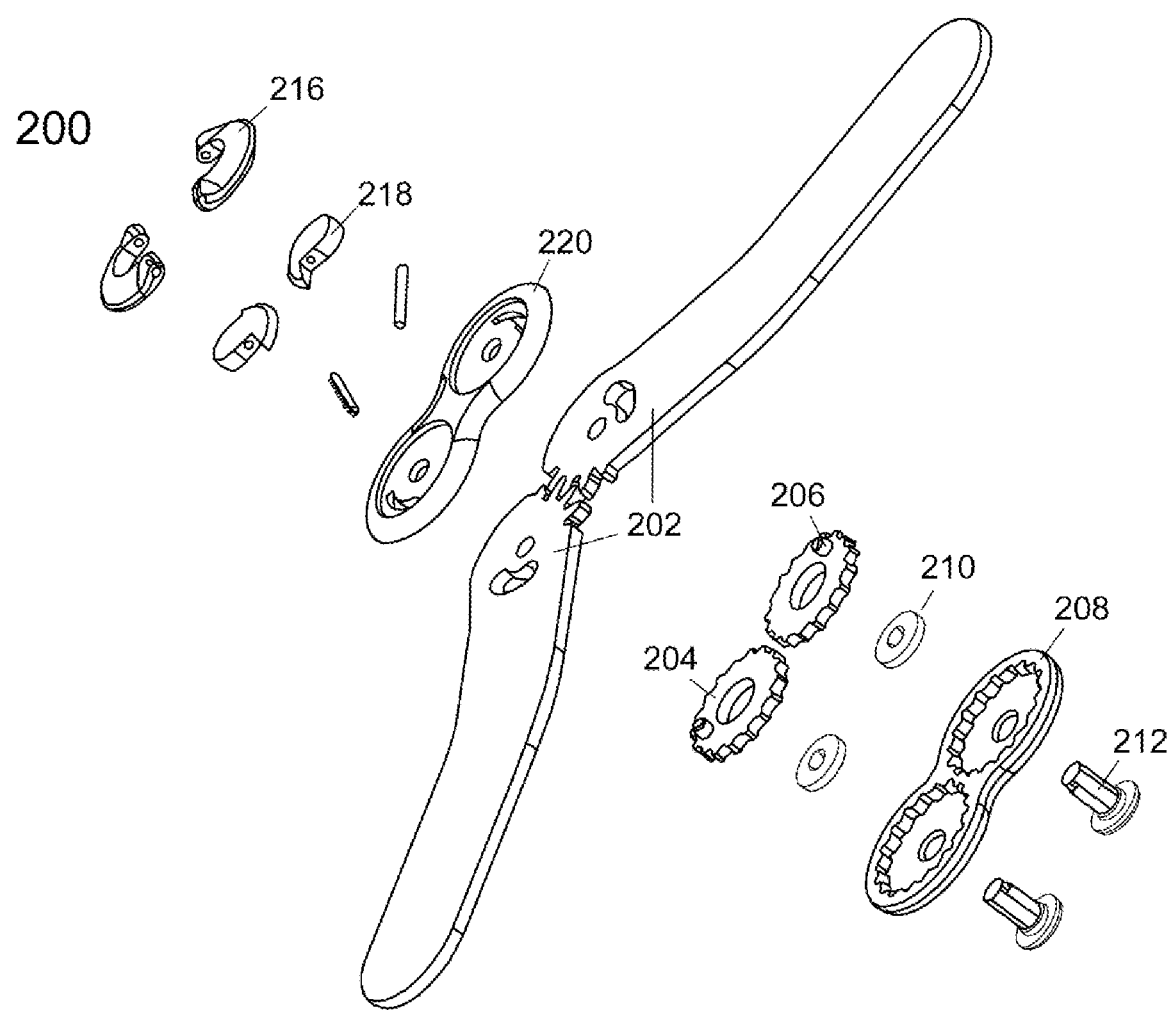
FIG. 2 is a front perspective of a dissected hinge brace system.

FIG. 2 depicts a front perspective of a dissected hinge brace system 200. The hinge brace system 200 may comprise at least two uprights 202 and at least two gears 204 on a first side of the uprights 202. Each of the gears 204 may comprise a limit marking 206. The limit marking 206 may extrude from the gear 204 and into a cavity of the upright 202 so as to prevent the upright 202 from travelling rotationally past the limit marking 206.

The gear 204 may be configured to rest inside a gear housing 208 that may prevent movement of the gear 204. The gear 204 may comprise an internal cavity that may be configured to receive a cam 210. The cam 210 may be configured to interface with a pin 212 that may perpendicularly pierce the gear 204. The pin 212 may be configured to turn the cam 210 causing the cam 210 to walk the gear 204 around the gear housing 208.

The hinge brace system 200 may further comprise a dial on a second side of the uprights 202 opposite the first side. The dial may comprise a dial flange 216 and a dial base 218. The dial may be configured to set into a housing cap 220 where the dial may be detachably coupled to the pin 212. The dial flange 216 may be configured to pivot substantially perpendicular to the housing cap 220 and cause the pin 212 to rotate the cam 210. The dial flange 216 may be further configured to turn rotationally about an axis of the pin 212 and rotating the cam 210 and subsequently the gear 204 to a plurality of positions that allow the limit marking 206 to provide different ranges of motion for the uprights 202.

Figure 3:
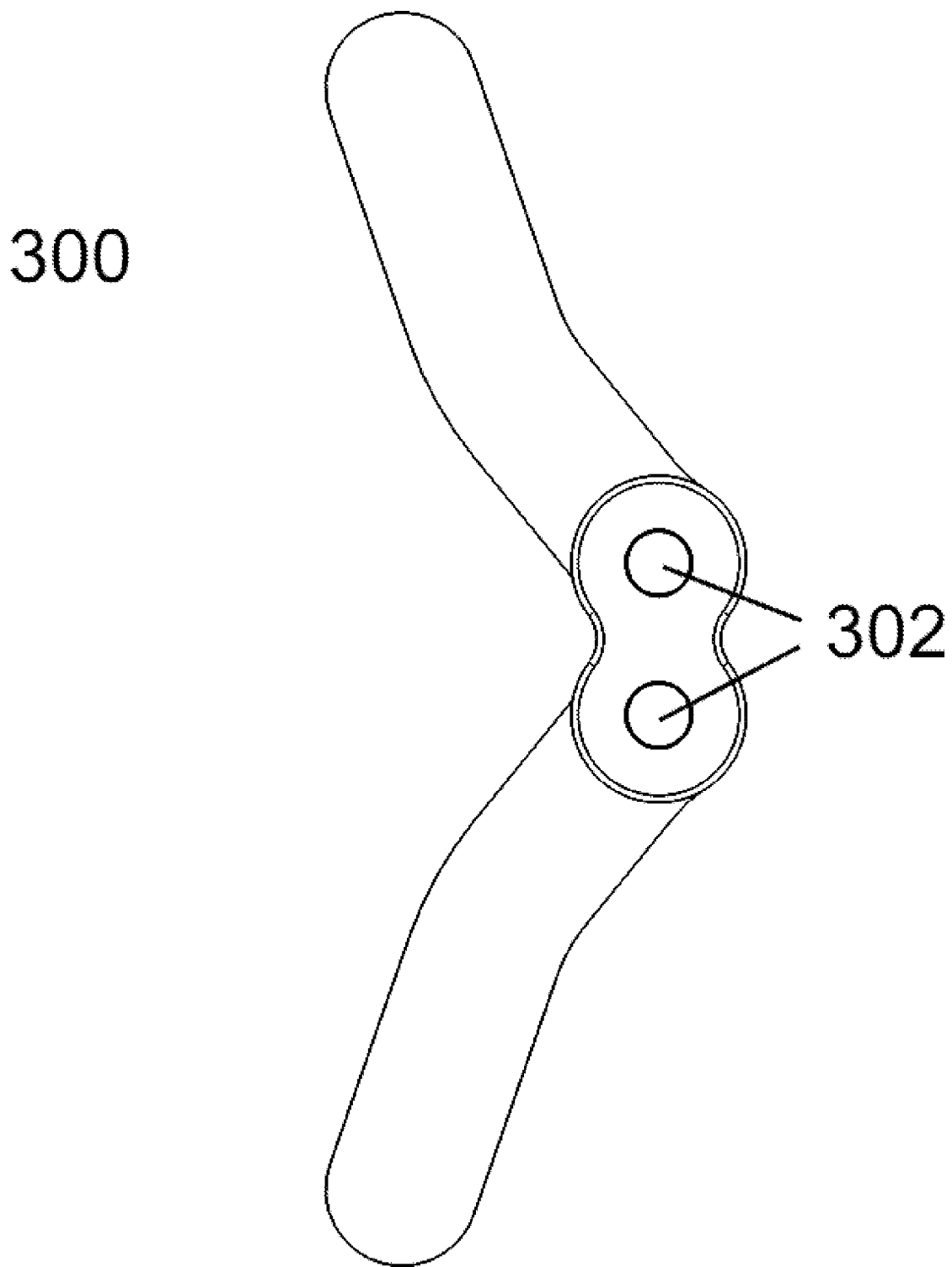
FIG. 3 is a rear perspective of a hinge brace system.

FIG. 3 depicts a rear perspective of a hinge brace system 300. The hinge brace system 300 may be the hinge brace system 200 of FIG. 2. The hinge brace system 300 may comprise at least two pins 302. One of ordinary skill in the art will recognize that a plurality of pin mechanisms may exist.

Figure 4:
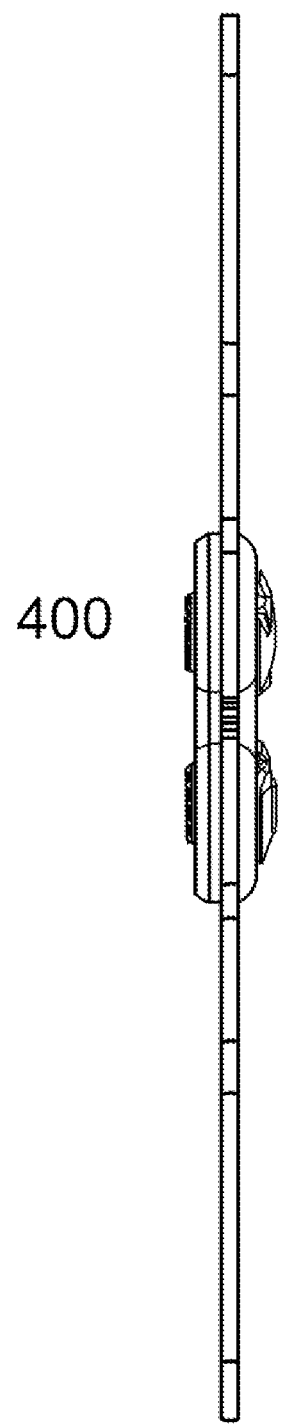
FIG. 4 is a side perspective of a hinge brace system.

FIG. 4 depicts a side perspective of a hinge brace system 400. The hinge brace system 400 may be the hinge brace system 200 of FIG. 2.

Figure 5:
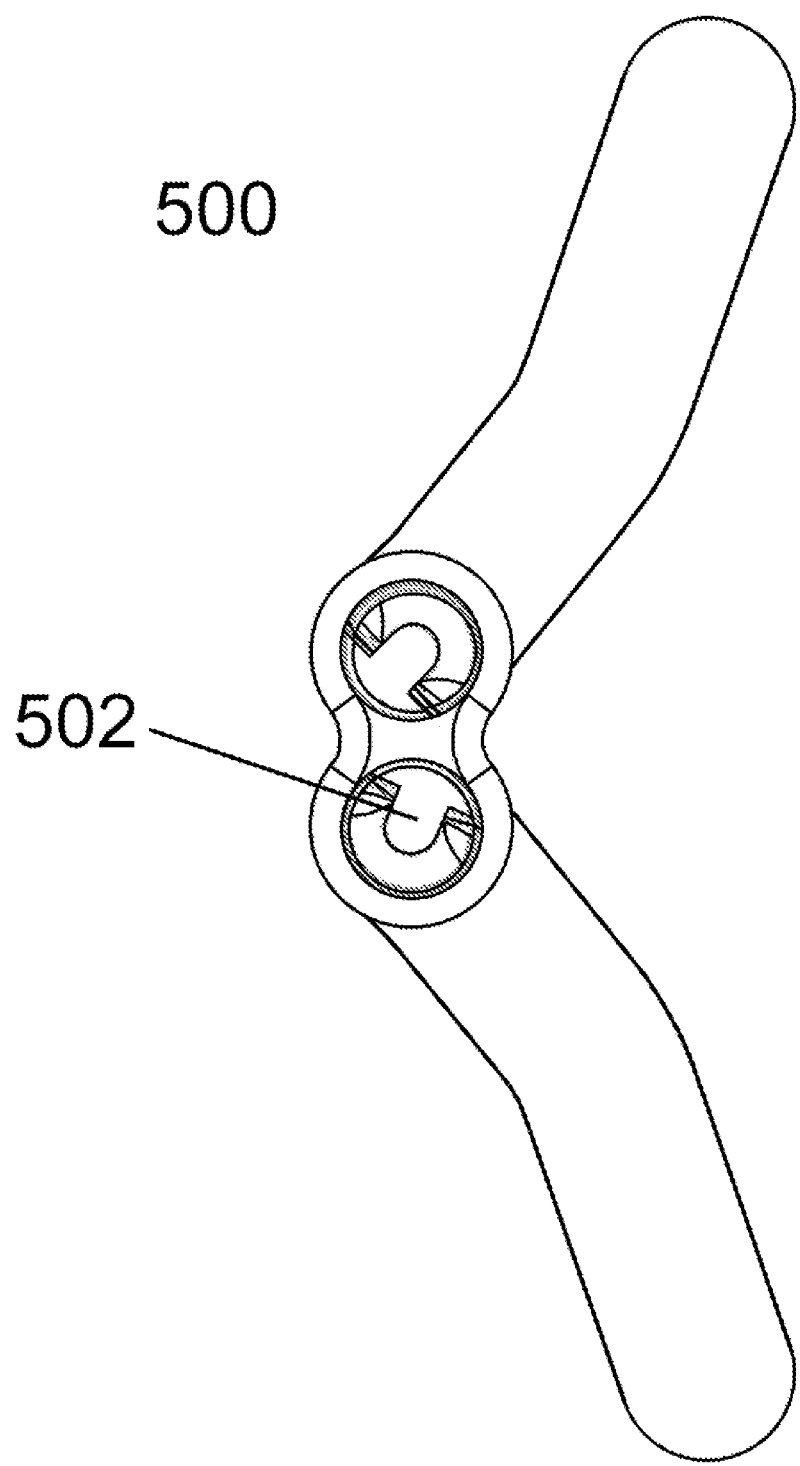
FIG. 5 is a front perspective of a hinge brace system.

FIG. 5 depicts a front perspective of a hinge brace system 500. The hinge brace system 500 may be the hinge brace system 200 of FIG. 2. The hinge brace system 500 may comprise at least two dials 502. One of ordinary skill in the art will appreciate that a plurality of adjustment knobs are recognized to perform dial functions.

Figure 6:
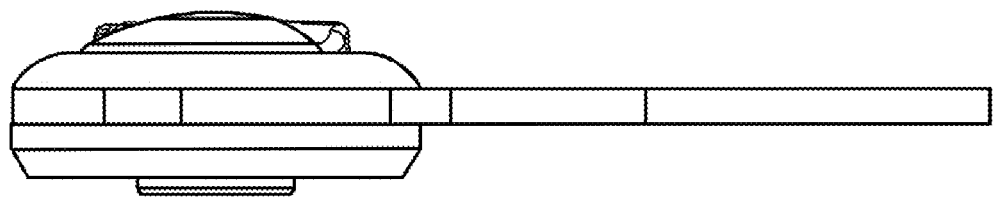
FIG. 6 is a side horizon perspective of a hinge brace system.

FIG. 6 depicts a side horizon perspective of a hinge brace system 600. The hinge brace system 600 may be the hinge brace system 200 of FIG. 2.

Figure 7:
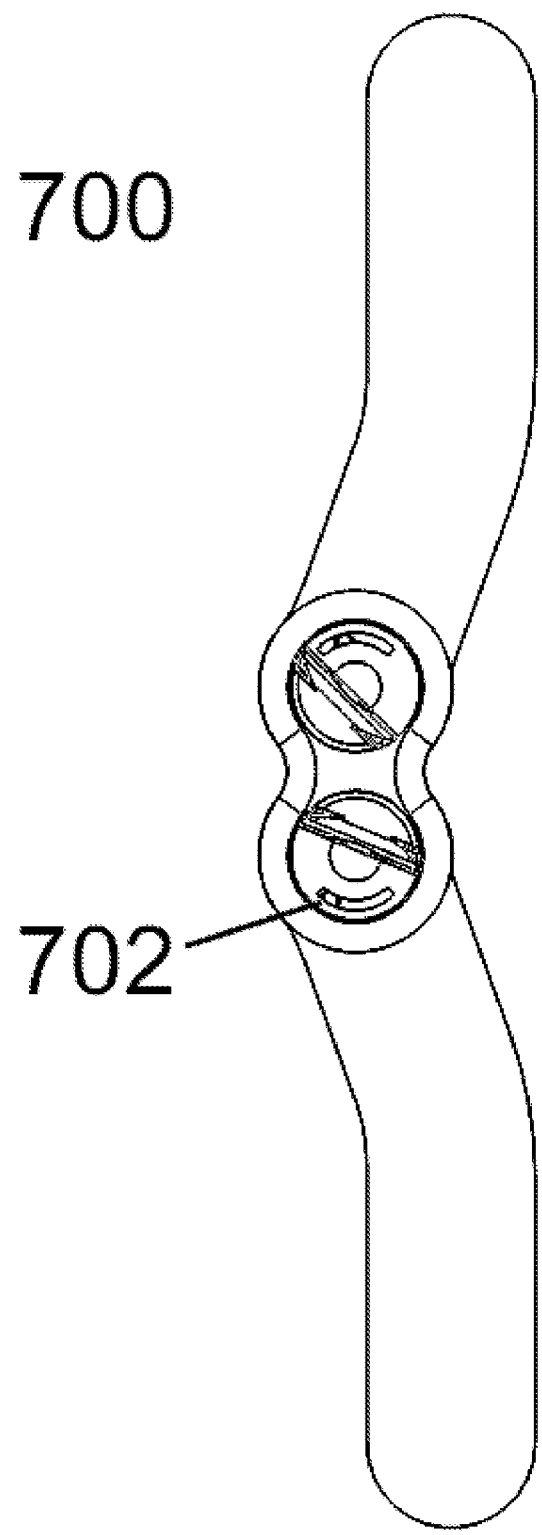
FIG. 7 is a front perspective view of a hinge brace system.

FIG. 7 depicts a front perspective view of a hinge brace system 700. The hinge brace system 700 may be the hinge brace system 200 of FIG. 2. The hinge brace system 700 may comprise at least two gears. Each of the gears may comprise a limit marking 702. One of ordinary skill in the art will appreciate that the limit marking 702 may comprise a plurality of visual aids such as, but not limited to, colored markings, estimated rotational degree markings, and physical extrusions. In another embodiment, the estimated rotational degree markings may be an estimated angle and may be printed on a housing cap such as the housing cap 220 of FIG. 2.

Figure 8:
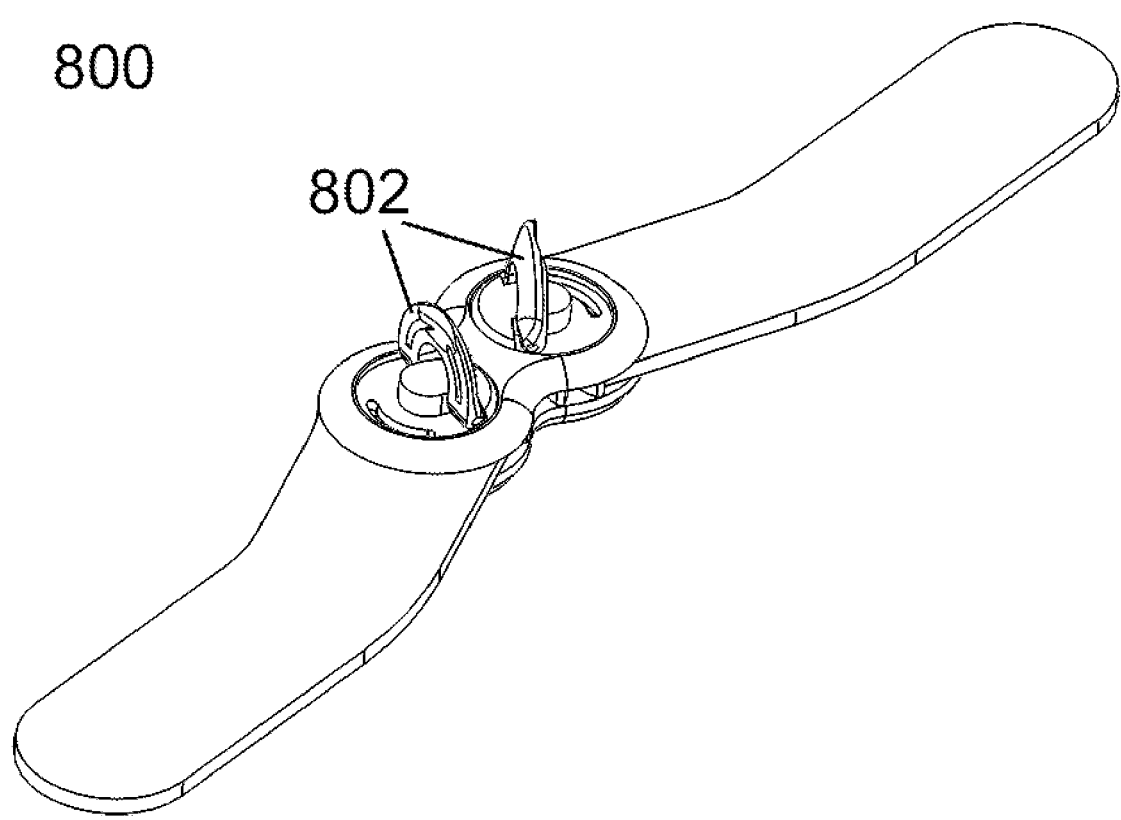
FIG. 8 is a perspective view of a hinge brace system.

FIG. 8 depicts a perspective view of a hinge brace system 800. The hinge brace system 800 may be the hinge brace system 200 of FIG. 2. The hinge brace system 800 may comprise a dial that comprises a dial base and a dial flange 802. In one embodiment, the dial flange 802 may be pivoted approximately ninety degrees to be substantially perpendicular to the hinge brace system 800. The pivoting of the dial flange 802 may allow a gear such as the gear 204 of FIG. 2 internal to the hinge brace system 800 to walk around an internal gear housing such as the gear housing 208 of FIG. 2. One of ordinary skill in the art will appreciate that a plurality of adjustment knob mechanisms may allow the internal gear to step about the internal gear housing.

Figure 9:
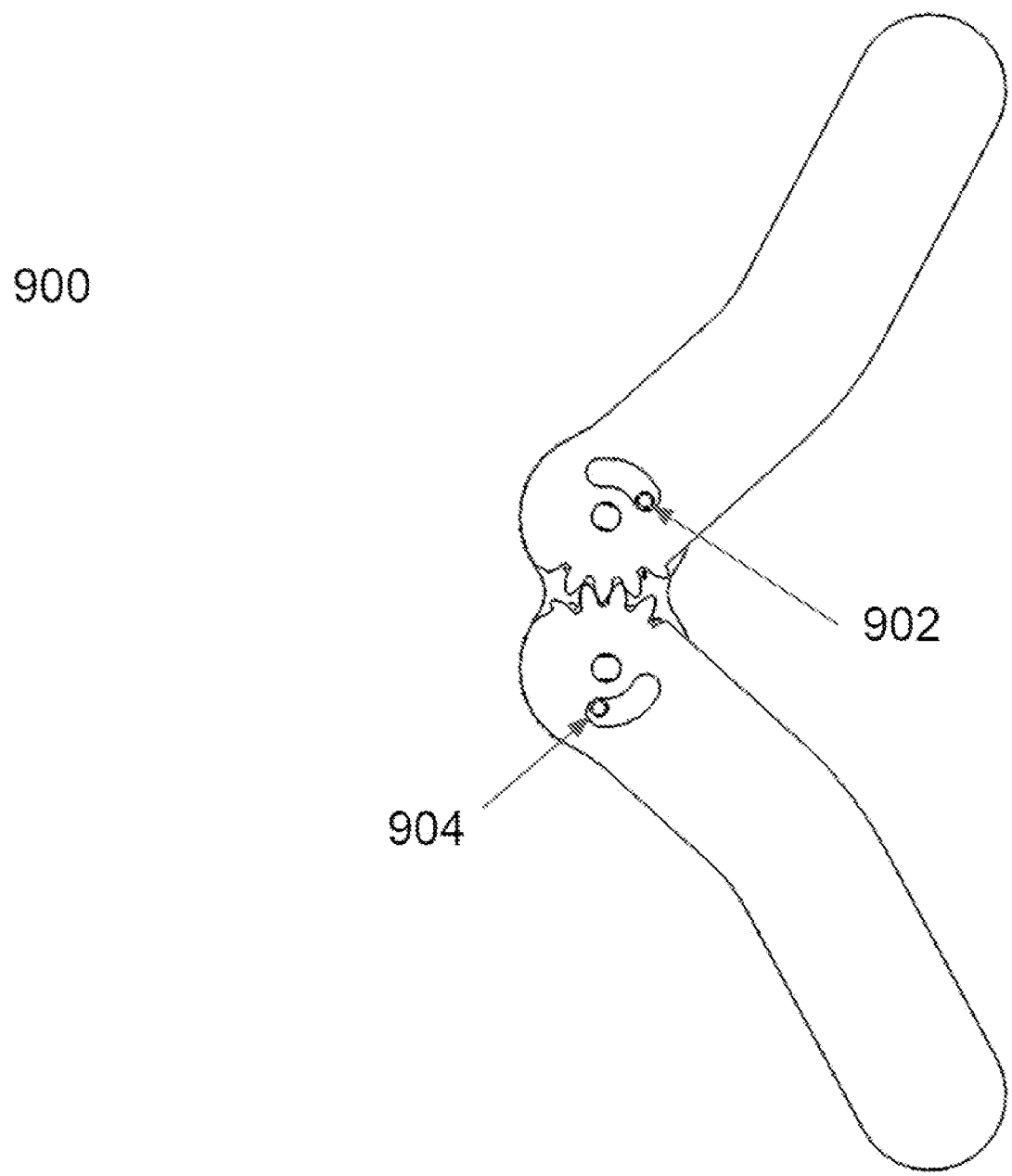
FIG. 9 is a front perspective view of a hinge brace system.

FIG. 9 depicts a front perspective view of a hinge brace system 900. The hinge brace system 900 may be the hinge brace system 200 of FIG. 2. The hinge brace system 900 may comprise at least two limit markings. A first limit marking may be configured to be an extension limit marking 902 that prevents the hinge brace system 900 from extending beyond a desired angle of extension. A second limit marking may be configured to be a flexion limit marking 904 that prevents the hinge brace system 900 from flexing beyond a desired angle of flexion. One of ordinary skill in the art will appreciate that FIG. 9 depicts an embodiment of a hinge brace system 900 that is configured to lock a joint in place and substantially preventing both flexion and extension beyond a fixed position.

Figure 10:
FIG. 10 is a perspective view of a hinge brace system.

FIG. 10 depicts a perspective view of a hinge brace system 1000. The hinge brace system 1000 may be the hinge brace system 900 of FIG. 9. The hinge brace system 1000 may reflect an extension limit marking and flexion limit marking such as the extension limit marking 902 and flexion limit marking 904 of FIG. 9 from a different view angle.

Figure 11:
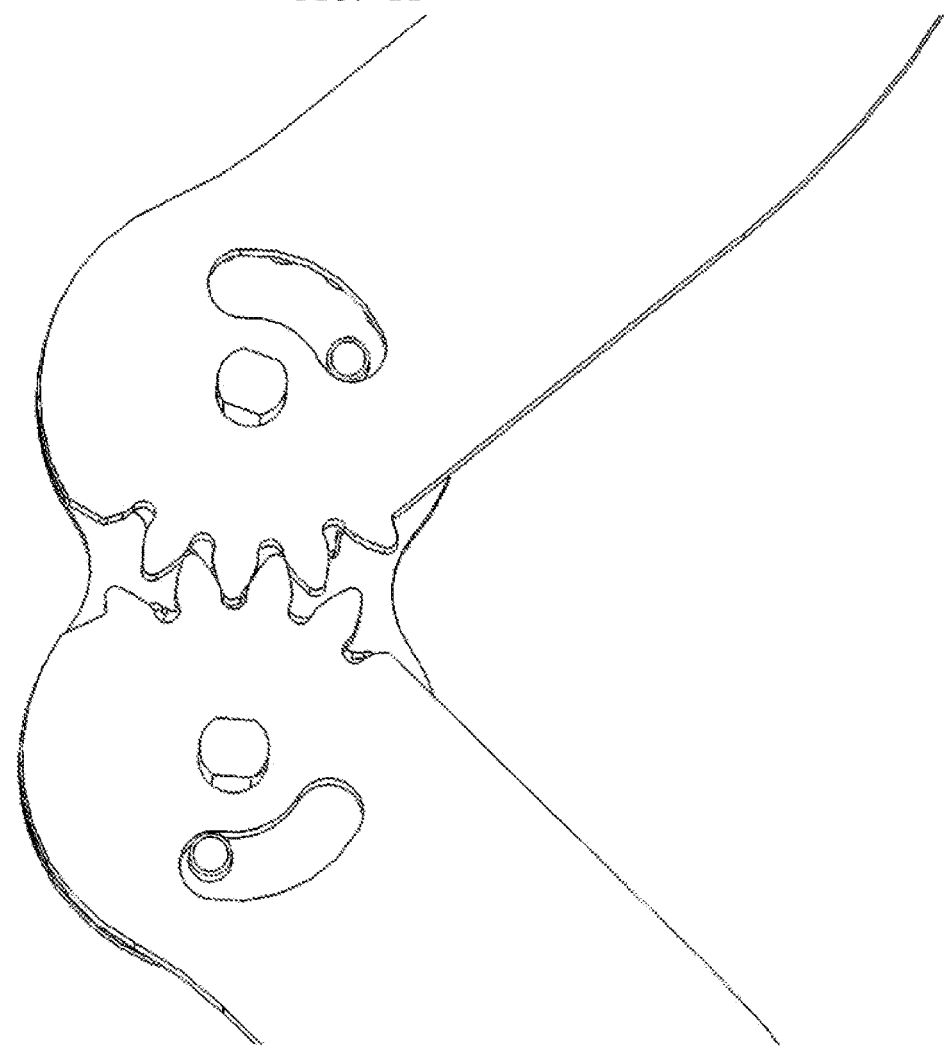
FIG. 11 is a perspective view of a joint of a hinge brace system.

FIG. 11 depicts a perspective view of a joint 1100 of a hinge brace system. The hinge brace system may be the hinge brace system 900 of FIG. 9. The joint 1100 may reflect an extension limit marking and flexion limit marking such as the extension limit marking 902 and flexion limit marking 904 of FIG. 9.

Figure 12:
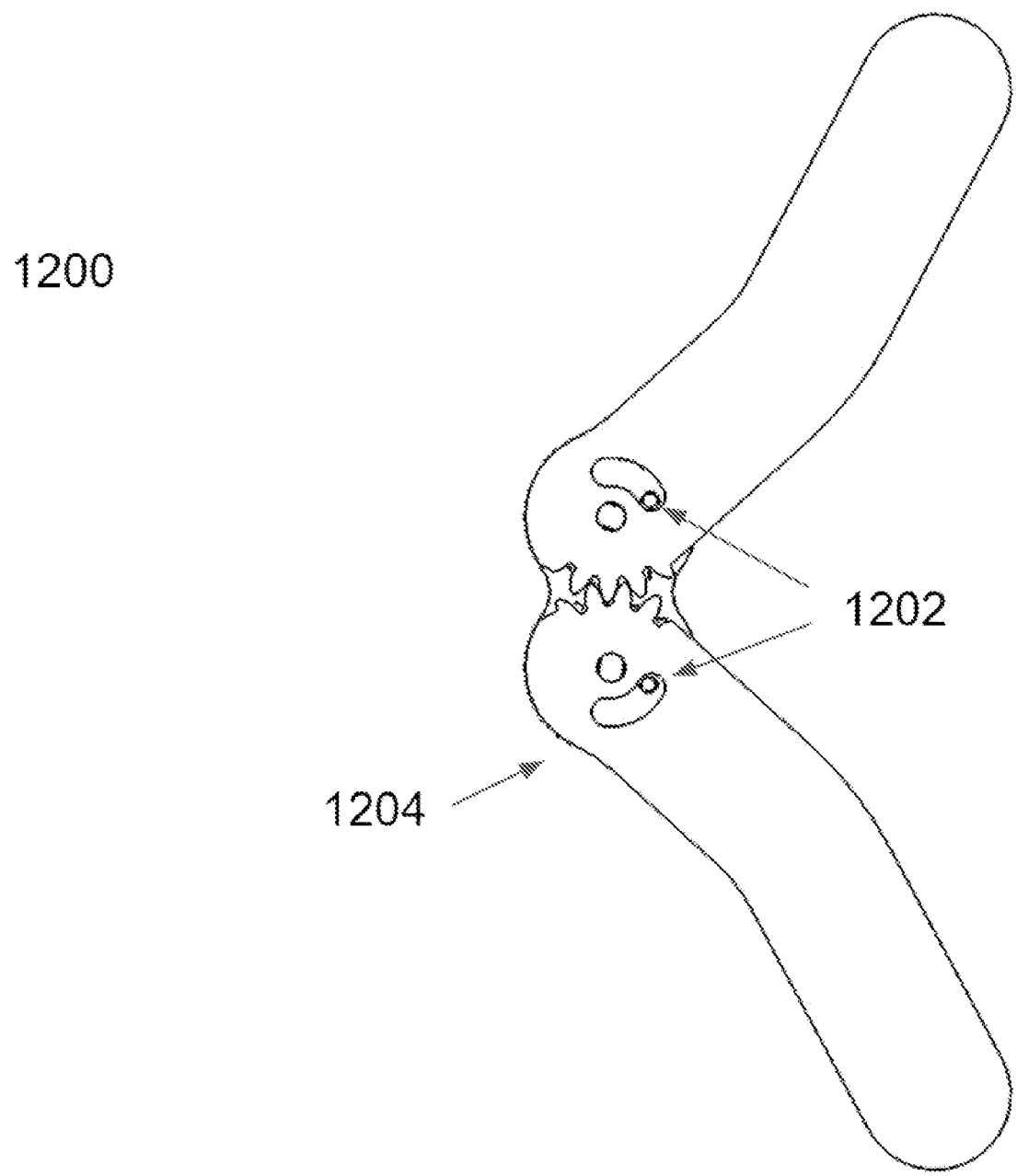
FIG. 12 is a perspective view of a hinge brace system.

FIG. 12 depicts a perspective view of a hinge brace system 1200. The hinge brace system 1200 may be the hinge brace system 200 of FIG. 2. The hinge brace system 1200 may be configured to comprise at least two limit markings 1202.

In one embodiment, the limit markings 1202 may be configured to stop movement in the same direction, for example, extension of the hinge brace system 1200. The limit markings 1202 may be configured to prevent extension beyond a desired angle of extension and combining provide substantially double a force of prevention. In this embodiment, the hinge brace system 1200 may comprise substantially unlimited flexion 1204 in response to the limit markings 1202. One of ordinary skill in the art will appreciate that flexion will be naturally limited as described further hereinbelow with reference to FIG. 14. One of ordinary skill in the art will also appreciate that the limit markings 1202 may conversely be configured to both prevent flexion beyond a desired angle of flexion in a similar manner to that of the extension in FIG. 12. Additionally, in one embodiment, the limit markings 1202 may be positioned to an outside of each of a slot of the uprights to prevent both flexion and extension thus immobilizing the joint (i.e., locked with no range of motion allowed).

Figure 13:
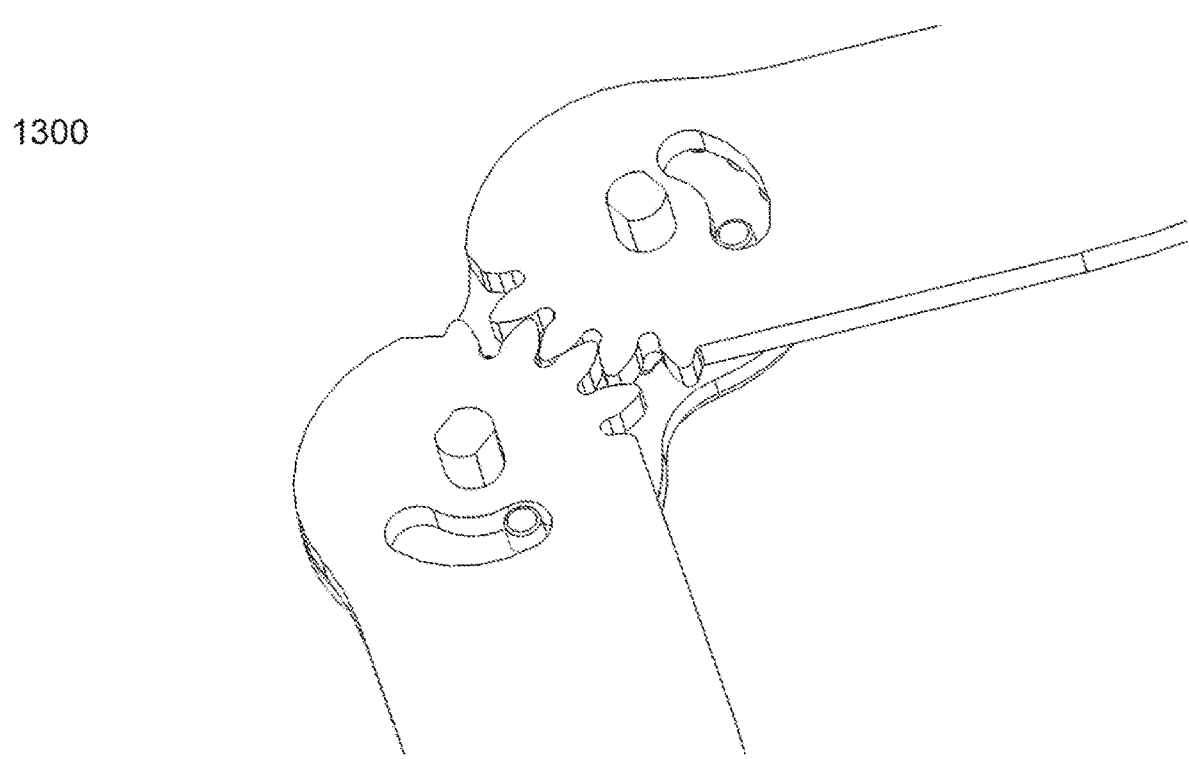
FIG. 13 is a perspective view of a joint of a hinge brace system.

FIG. 13 depicts a perspective view of a joint 1300 of a hinge brace system. The hinge brace system may be the hinge brace system 1200 of FIG. 12. The joint 1300 may reflect limit markings such as the limit markings 1202 of FIG. 12.

Figure 14:
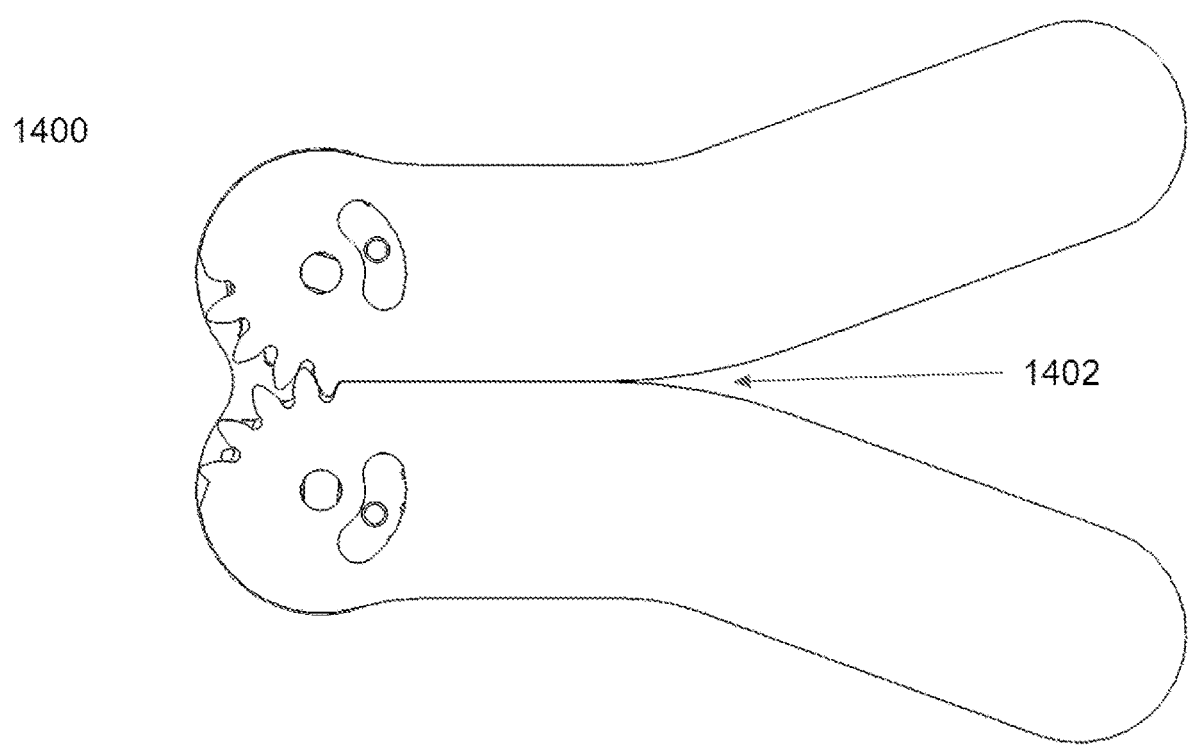
FIG. 14 is a perspective view of a hinge brace system.

FIG. 14 depicts a perspective view of a hinge brace system 1400. The hinge brace system 1400 may be the hinge brace system 1200 of FIG. 12. The hinge brace system 1400 may reflect limit markings such as the limit markings 1202 of FIG. 12. The hinge brace system 1400 may comprise a natural flexion limit 1402 as a result of uprights of the hinge brace system 1400 interfering with flexion beyond a point of contact.

Figure 15:
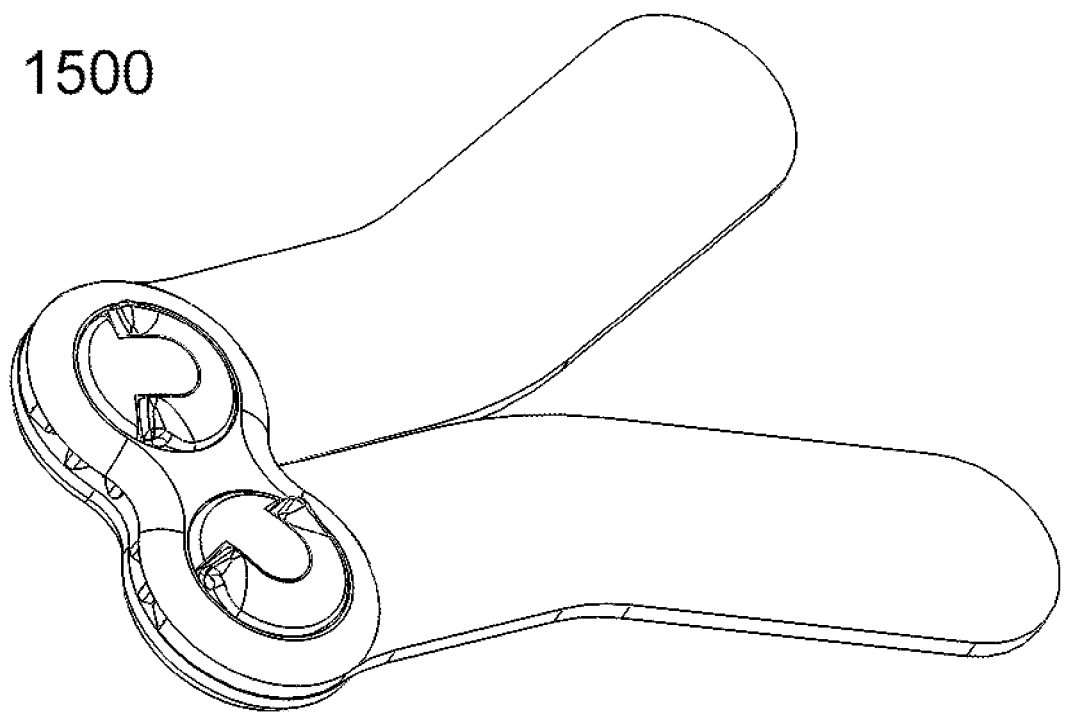
FIG. 15 is a perspective view of a hinge brace system.

FIG. 15 depicts a perspective view of a hinge brace system 1500. The hinge brace system 1500 may be the hinge brace system 1200 of FIG. 12.

Figure 16:
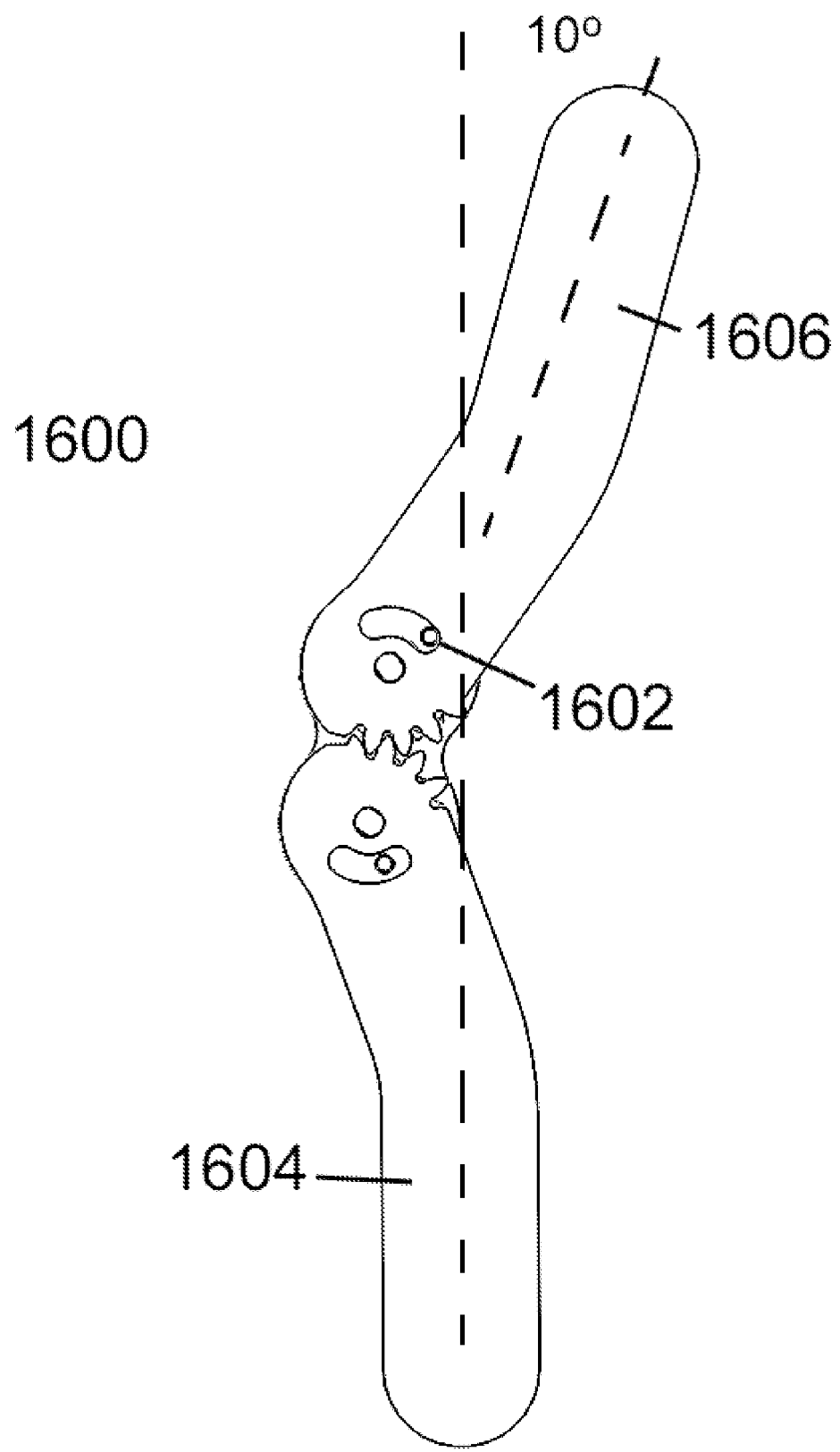
FIG. 16 is a perspective view of a hinge brace system.

FIG. 16 depicts a perspective view of a hinge brace system 1600. The hinge brace system 1600 may be the hinge brace system 200 of FIG. 2. The hinge brace system 1600 may comprise an extension limit marking 1602. In one embodiment, the hinge brace system 1600 may be configured to prevent extension beyond approximately ten degrees of extension. The approximately ten degrees of extension may be represented by a first upright axis 1604 and a second upright extension limit 1606 at approximately ten degrees from the first upright axis 1604. The extension limit marking 1602 is configured to prevent extension of the second upright extension limit 1606 towards a line substantially more parallel to the first upright axis 1604. One of ordinary skill in the art will appreciate that a dial and gear such as those described herein will allow a user to alter the extension limit marking 1602 to a desired angle of extension.

Figure 17:
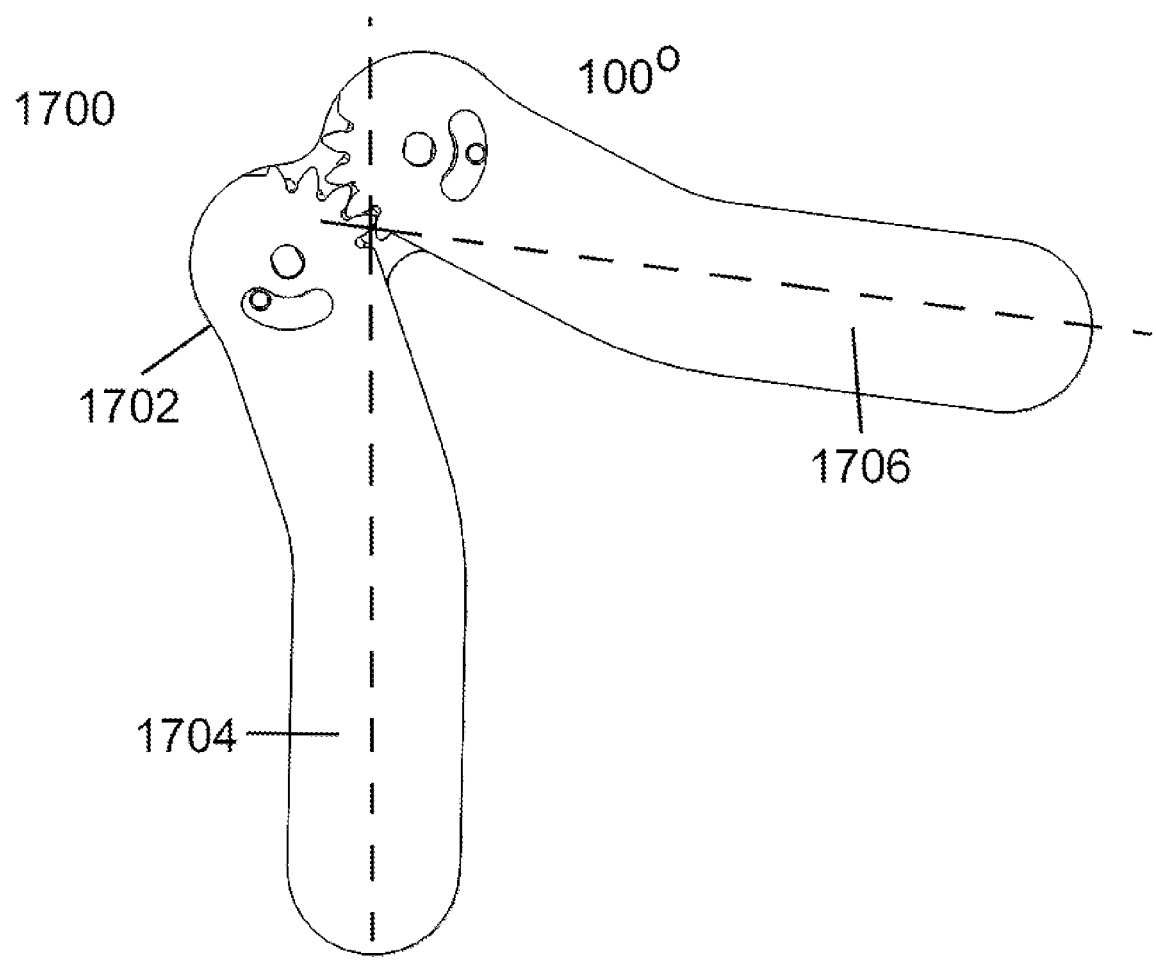
FIG. 17 is a perspective view of a hinge brace system.

FIG. 17 depicts a perspective view of a hinge brace system 1700. The hinge brace system 1700 may be the hinge brace system 200 of FIG. 2. The hinge brace system 1700 may comprise a flexion limit marking 1702. In one embodiment, the hinge brace system 1700 may be configured to prevent flexion beyond approximately one hundred degrees of flexion. The approximately one hundred degrees of flexion may be represented by a first upright axis 1704 and a second upright flexion limit 1706 at approximately one hundred degrees from the first upright axis 1704. The flexion limit marking 1702 is configured to prevent flexion of the second upright flexion limit 1706 towards a first upright axis 1704 and contact with a corresponding first upright. One of ordinary skill in the art will appreciate that a dial and gear such as those described herein will allow a user to alter the flexion limit marking 1702 to a desired angle of flexion.

Figure 18:
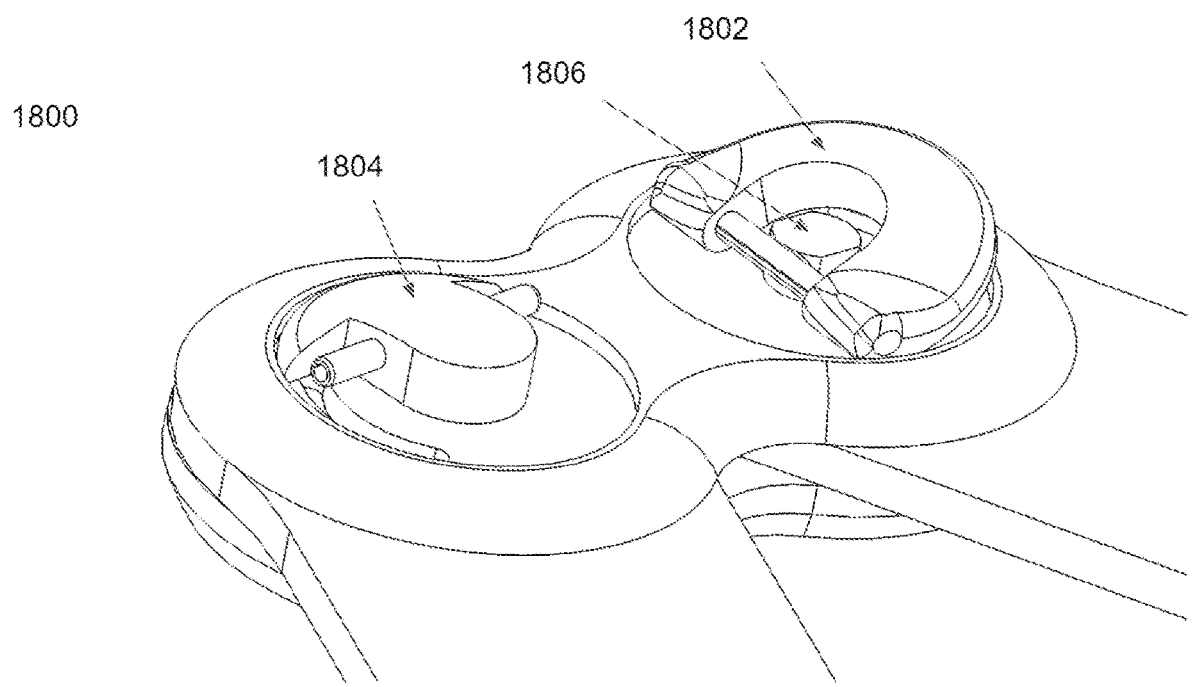
FIG. 18 is a perspective view of a joint of a hinge brace system.

FIG. 18 depicts a perspective view of a joint 1800 of a hinge brace system. The hinge brace system may be the hinge brace system 200 of FIG. 2. The hinge brace system may comprise a dial. The dial may comprise a dial flange 1802 and a dial base 1804. The dial flange 1802 may interact with a pin 1806 in response to a bar of the dial flange 1802 resting in a groove of the pin 1806. As such, one of ordinary skill in the art will appreciate that rotation of the dial flange 1802 will result in rotation of the pin 1806.

Figure 19:
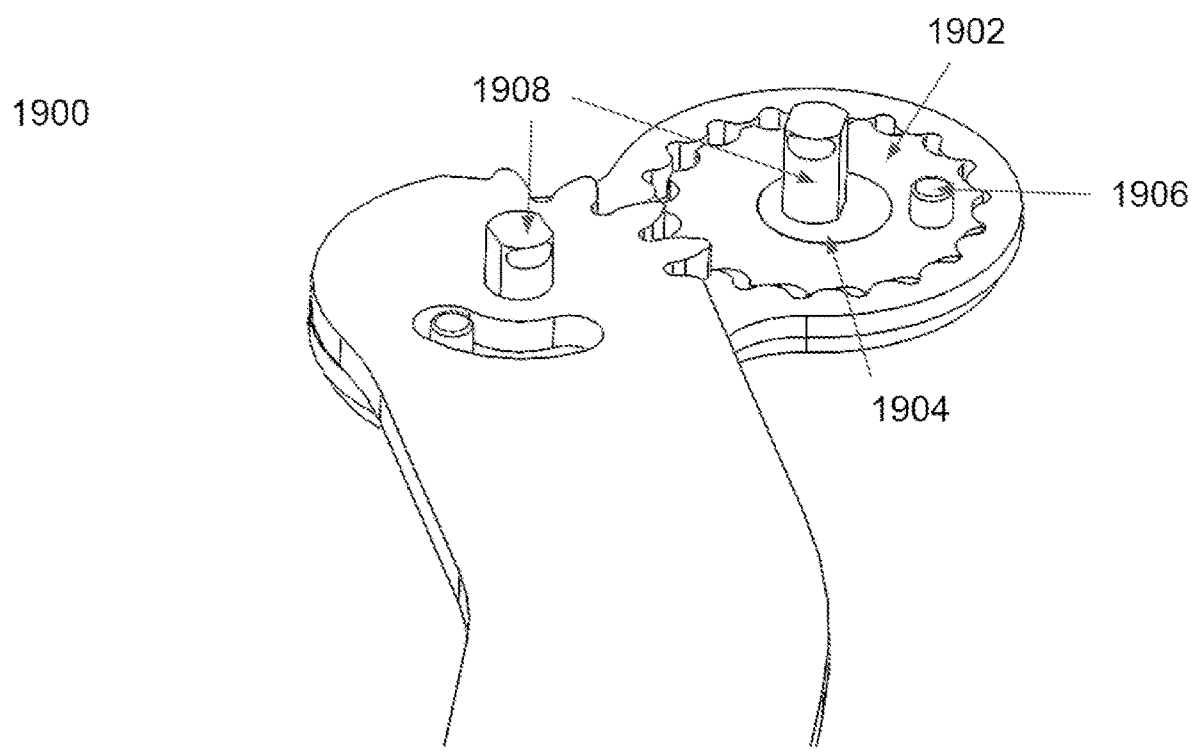
FIG. 19 is a perspective view of a dissected joint of a hinge brace system.

FIG. 19 depicts a perspective view of a dissected joint 1900 of a hinge brace system. The hinge brace system may be the hinge brace system 200 of FIG. 2. The hinge brace system may comprise a gear 1902, a cam 1904, a limit marking 1906 extruding from the gear 1902, and a pin 1908 running through a center of the cam 1904. As such, one of ordinary skill in the art will appreciate that rotation of the pin 1906 will result in rotation of the cam 1904, the gear 1902, and the limit marking 1906.

Figure 20:
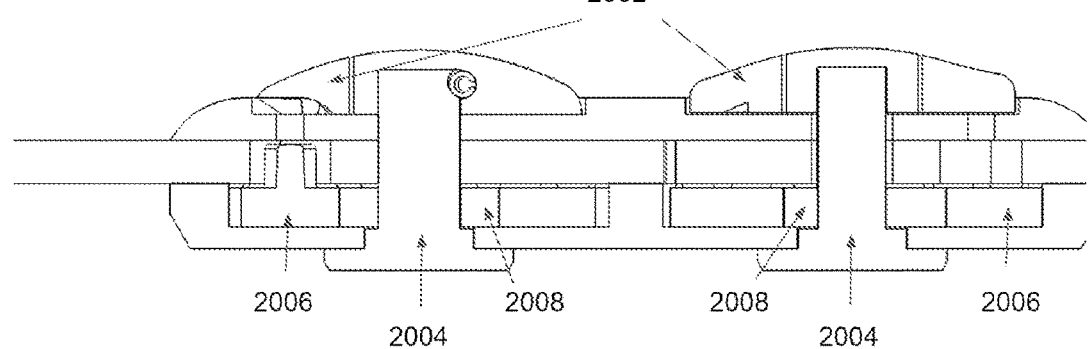
FIG. 20 is a cross-sectional perspective view of a joint of a hinge brace system.

FIG. 20 depicts a cross-sectional perspective view of a joint 2000 of a hinge brace system. The hinge brace system may be the hinge brace system 200 of FIG. 2. The hinge brace system may comprise a dial flange 2002, a pin 2004, a gear 2006, and a cam 2008.

Figure 21:
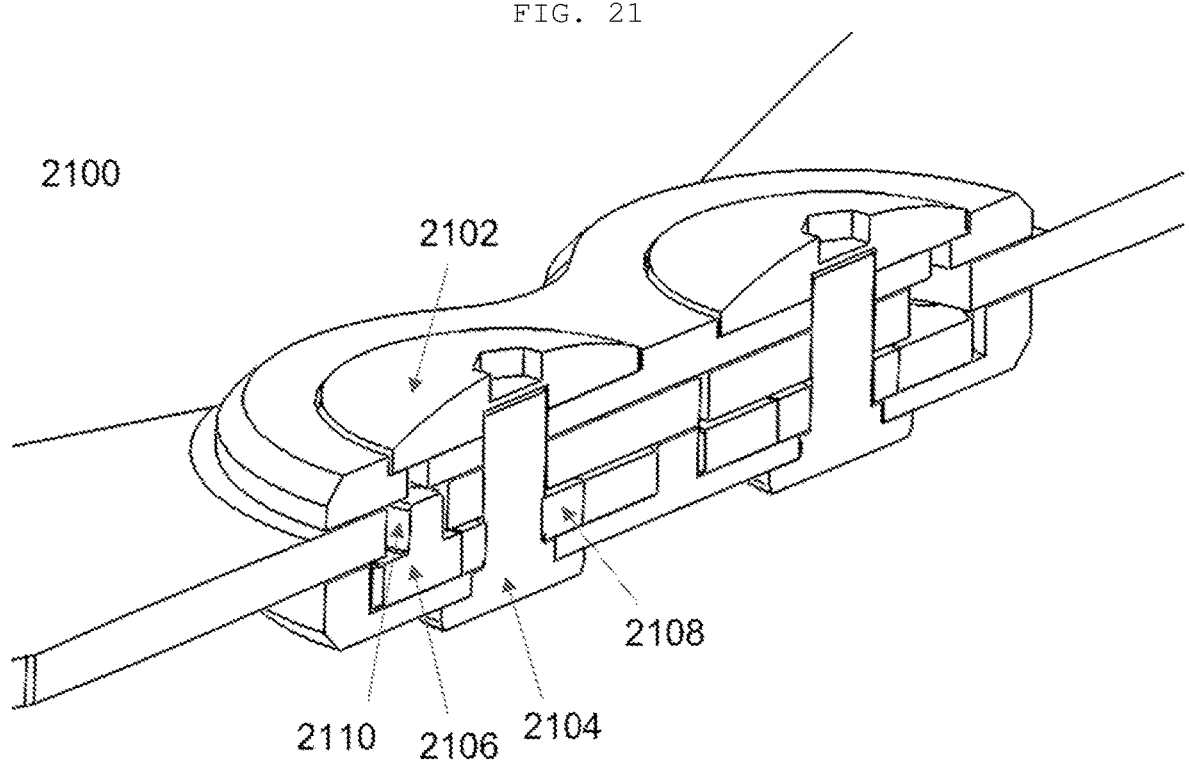
FIG. 21 is a cross-sectional perspective view of a joint of a hinge brace system with a hex-key cap 2102.

FIG. 21 depicts a cross-sectional perspective view of a joint 2100 of an alternative embodiment of the hinge brace system. The hinge brace system may be the hinge brace system 200 of FIG. 2. The alternative embodiment of the hinge brace system may comprise a hex key cap 2102, a pin 2104, a gear 2106, a cam 2108, and a limit marking 2110.

Figure 22:
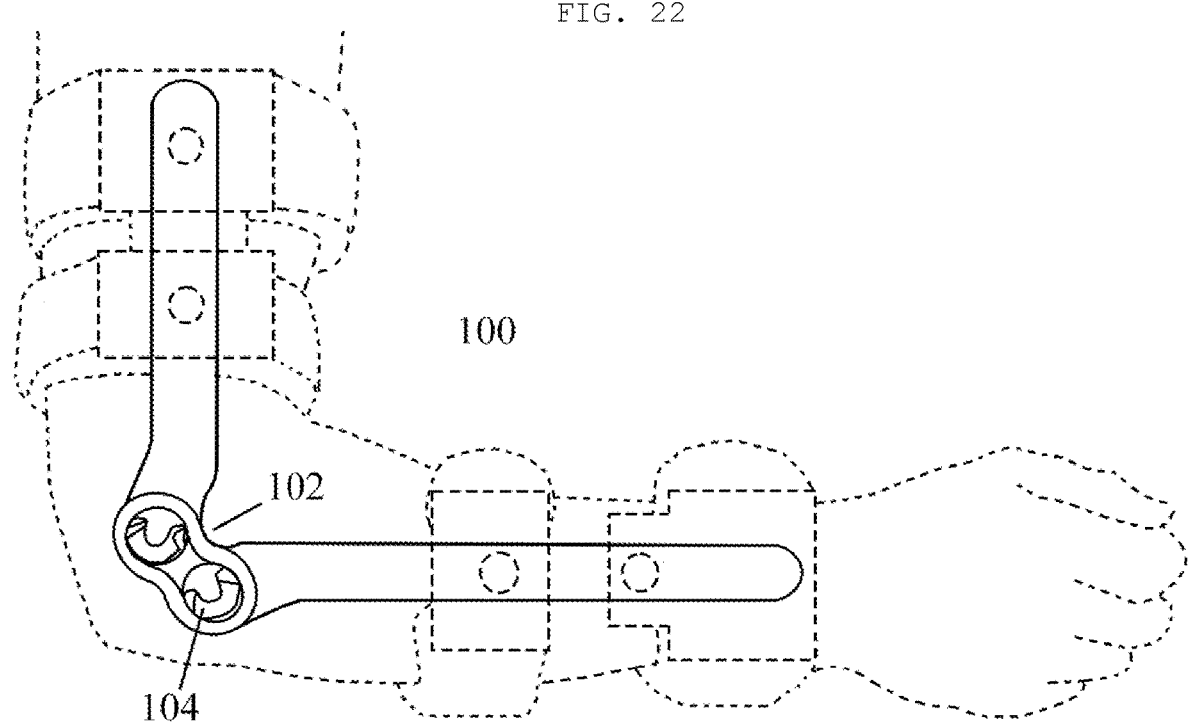
FIG. 22 is a side view of a hinge brace system on an arm.
Figure 23:
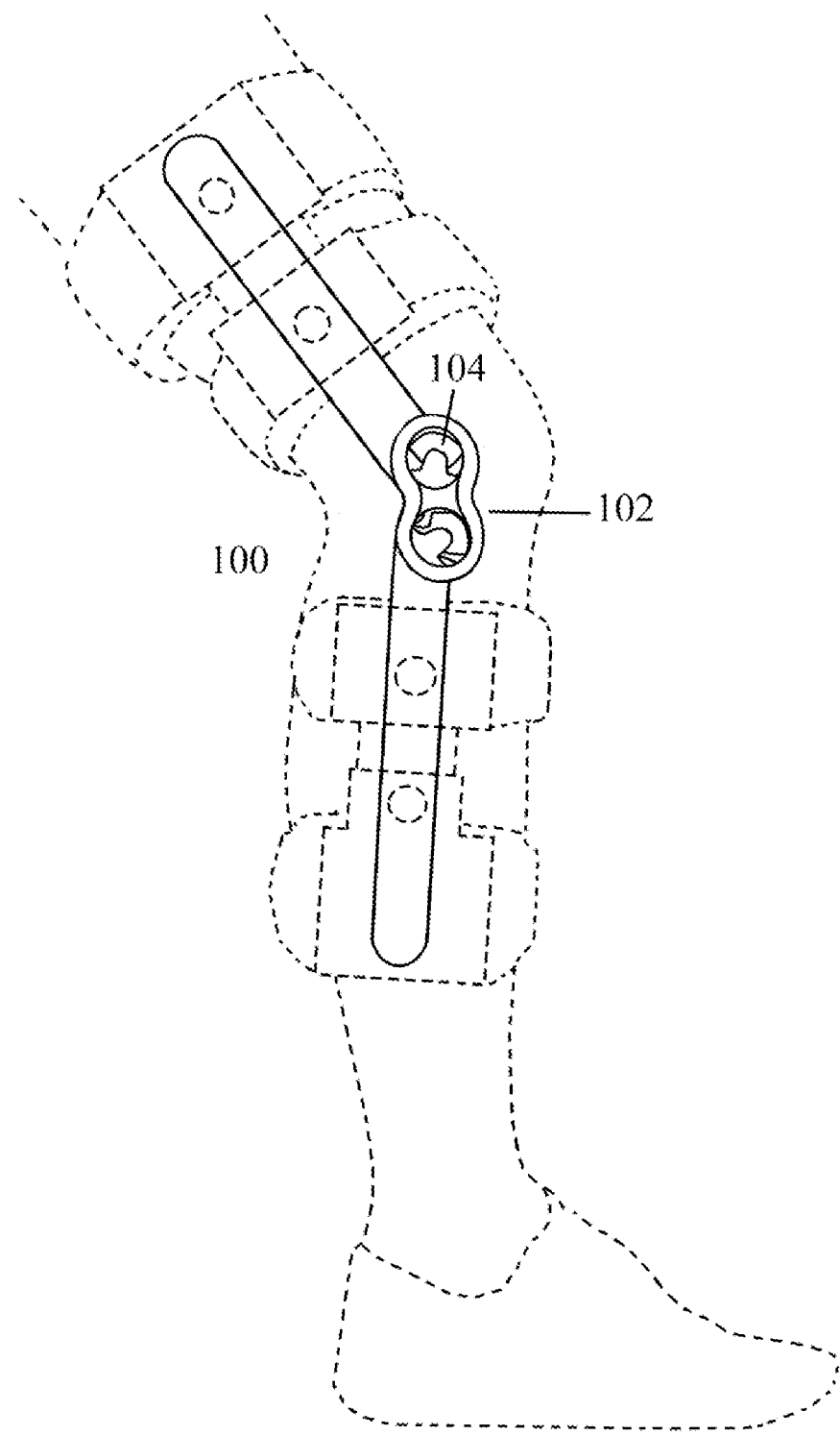
FIG. 23 is a side view of a hinge brace system on a leg.
Figure 24:
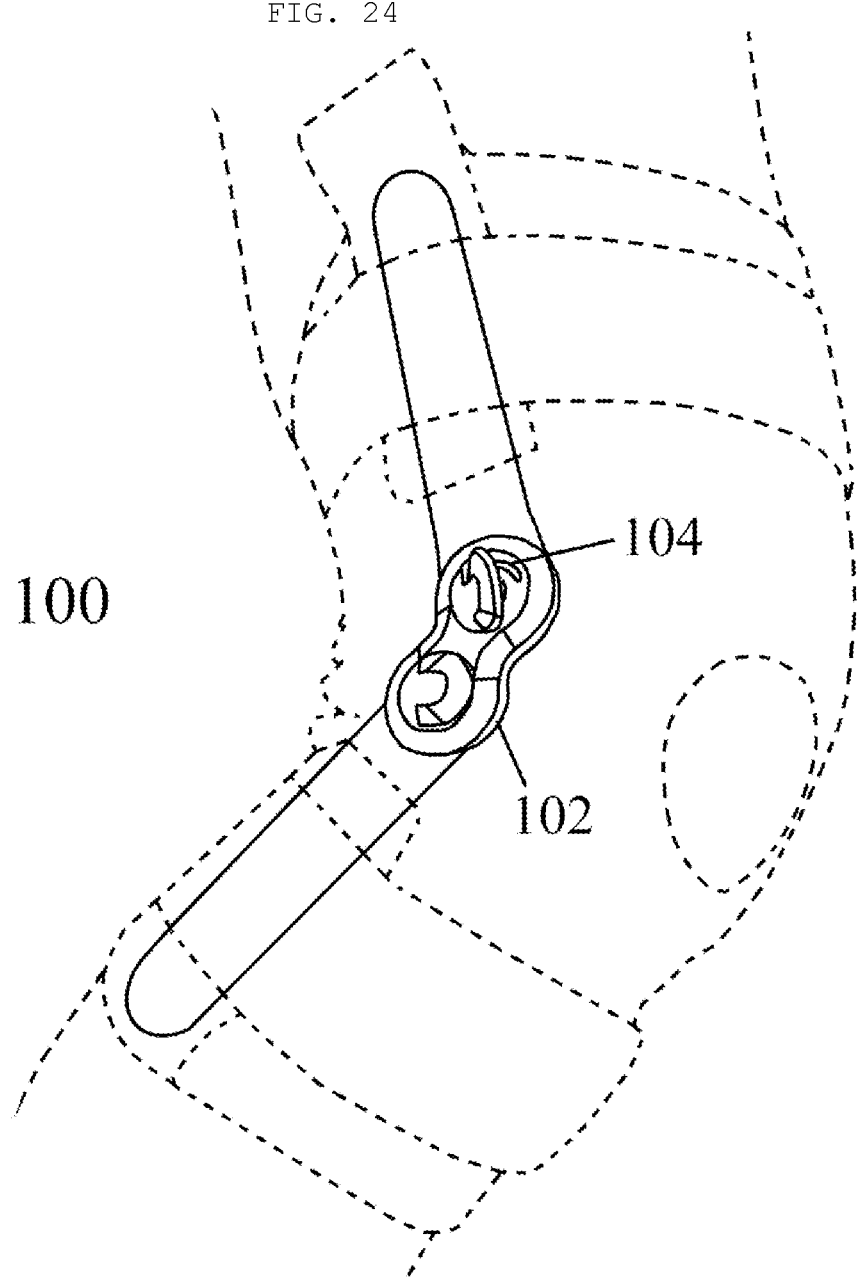
FIG. 24 is an orthogonal view of a hinge brace system on a knee.

FIG. 22 depicts a hinge brace system 100 on an arm. FIG. 23 depicts a hinge brace system 100 on a leg. FIG. 24 depicts a hinge brace system on a knee.

In one embodiment, the hinge brace system may comprise only one dial mechanism. In one embodiment, the dial mechanism may be a tool-type interface. In one embodiment, the tool-type interface may comprise a pin comprising a hex key or similar tool interfacing cavity.

In one embodiment, the hinge brace system may be configured to be molded to a patient's body surrounding an injured anatomical joint of the patient as depicted by, but not limited to, FIGS. 22-24.

In one embodiment, the hinge brace system may comprise materials consisting of a carbon fiber variant such as, but not limited to, RTP287. In one embodiment, other materials of the hinge brace system may consist of a Zytel ST801 or other similar material. One of ordinary skill in the art will appreciate that a plurality of similar materials exists with comparable characteristics. Additionally, in other embodiments, the hinge brace system may comprise such materials as, but not limited to, plastic, aluminum, and other common hinge brace materials.

Some of the illustrative aspects of the present invention may be advantageous in solving the problems herein described and other problems not discussed which are discoverable by a skilled artisan.

While the above description contains much specificity, these should not be construed as limitations on the scope of any embodiment, but as exemplifications of the presented embodiments thereof. Many other ramifications and variations are possible within the teachings of the various embodiments. While the invention has been described with reference to exemplary embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best or only mode contemplated for carrying out this invention. Also, in the drawings and the description, there have been disclosed exemplary embodiments of the invention and, although specific terms may have been employed, they are unless otherwise stated used in a generic and descriptive sense only and not for purposes of limitation, the scope of the invention therefore not being so limited. Moreover, the use of the terms first, second, etc. do not denote any order or importance, but rather the terms first, second, etc. are used to distinguish one element from another. Furthermore, the use of the terms a, an, etc. do not denote a limitation of quantity, but rather denote the presence of at least one of the referenced items.

A legend of components discussed herein follows:
Hinge Brace System 100
Joint 102
Dial 104
Hinge Brace System 200
Upright 202

Gear 204
Limit Marking 206
Gear Housing 208
Cam 210
Pin 212
Dial Flange 216
Dial Base 218
Housing Cap 220
Hinge Brace System 300
Pin 302
Hinge Brace System 400
Hinge Brace System 500
Dial 502
Hinge Brace System 600
Hinge Brace System 700
Limit Marking 702
Hinge Brace System 800
Dial Flange 802
Hinge Brace System 900
Extension Limit Marking 902
Flexion Limit Marking 904
Hinge Brace System 1000
Joint 1100
Hinge Brace System 1200
Limit Marking 1202
Unlimited Flexion 1204
Joint 1300
Hinge Brace System 1400
Flexion Limit 1402
Hinge Brace System 1500
Hinge Brace System 1600
Extension Limit Marking 1602
First Upright Axis 1604
Second Upright Extension Limit 1606
Hinge Brace System 1700
Flexion Limit Marking 1702
First Upright Axis 1704
Second Upright Flexion Limit 1706
Joint 1800
Dial Flange 1802
Dial Base 1804
Pin 1806
Joint 1900
Gear 1902
Cam 1904
Limit Marking 1906
Pin 1908
Joint 2000
Dial Flange 2002
Pin 2004
Gear 2006
Cam 2008
Joint 2100
Hex-Key Cap, 2102
Pin 2104
Gear 2106
Cam 2108
Limit Marking 2110

The inventor claims:

1. A hinge brace system, comprising:
a first upright comprising gear teeth on an end internal to a joint of the hinge brace system;
a second upright comprising gear teeth on an end internal to the joint of the hinge brace system, the gear teeth of the second upright meshed with the gear teeth of the first upright;
a gear, a cam, and a pin associated with each of the first upright and second upright, the gears comprising an internal cavity configured to receive the cams, and the cams comprising another internal cavity configured to receive the pins, wherein the gear, cam, and pin are internal to a gear housing; and
a dial assembly opposite the gear housing, the dial assembly comprising a dial base and a dial flange, the dial flange configured to rotatably step the cam, causing the cam to step the gear about the gear housing;
wherein the gear further comprises a limit marking, the limit marking extruding from the gear into a slot of the upright and preventing the upright from travelling beyond a desired angle, the angle preventing rotation of the hinge brace system in at least one of extension and flexion;
wherein the dial flange is configured to be pivoted substantially perpendicular to the hinge brace system, wherein the pivoting allows a user to rotate the dial flange that cause the pin, the cam, and the gear to rotationally travel about the gear housing, wherein the gear rotationally travelling internal the gear housing causes the limit marking to rotate to desired position to prevent at least one of extension and flexion.

2. The hinge brace system according to claim 1, wherein the first limit marking associated with the first gear and the first upright is configured to limit extension of the joint, and wherein the second limit marking associated with the second gear and the second upright is configured to limit flexion of the joint.

3. The hinge brace system according to claim 2, wherein the joint of the hinge brace system may be configured to freely rotate between the extension limit and the flexion limit.

4. The hinge brace system according to claim 2, wherein the first limit marking and second limit marking are configured to prevent substantially any flexion and extension and substantially locking the hinge brace system to a desired angle with substantially no range-of-motion.

5. The hinge brace system according to claim 1, wherein the first limit marking and second limit marking are each configured to limit extension of the joint, and wherein contact of the first upright and the second upright are configured to provide a substantially natural limit to flexion of the joint.

6. The hinge brace system according to claim 5, wherein the joint of the hinge brace system may be configured to freely rotate between the extension limit and the natural limit to flexion caused by at least one of contact of the first upright and the second upright and a limit of human anatomy.

7. The hinge brace system, comprising:
a first upright comprising gear teeth on an end internal to a joint of the hinge brace system;
a second upright comprising gear teeth on an end internal to the joint of the hinge brace system, the gear teeth of the second upright meshed with the gear teeth of the first upright;
a gear, a cam, and a pin associated with each of the first upright and second upright, the gears comprising an internal cavity configured to receive the cams, and the cams comprising another internal cavity configured to receive the pins, wherein the gear, cam, and pin are internal to a gear housing; and
a dial assembly opposite the gear housing, the dial assembly comprising a dial base and a dial flange, the dial flange configured to rotatably step the cam, causing the cam to step the gear about the gear housing;

wherein the gear further comprises a limit marking, the limit marking extruding from the gear into a slot of the upright and preventing the upright from travelling beyond a desired angle, the angle preventing rotation of the hinge brace system in at least one of extension and flexion;

wherein the pin comprises a tool interfacing cavity, and wherein the pin is configured to be directly rotated by a user with a tool interfacing with the tool interfacing cavity.

8. The hinge brace system according to claim 7, wherein the tool interfacing cavity comprises a hex key.

9. The hinge brace system according to claim 1, wherein the limit marking comprises a colored marking visible to a user.

10. The hinge brace system according to claim 1, wherein the gear housing comprises numbered degree markings corresponding to an angle of the limit marking.

11. The hinge brace system according to claim 1, further comprising a housing cap configured to receive the dial in a stored position.

12. The hinge brace system according to claim 1, wherein the first upright and second upright consist of a carbon fiber variant.

13. The hinge brace system according to claim 1, wherein the first upright and second upright may be configured to be molded to a patient's body surrounding an injured anatomical joint of the patient.

14. The hinge brace system according to claim 1, wherein the first limit marking and second limit marking are each configured to limit flexion of the joint, and wherein contact of the first upright and the second upright are configured to provide a substantially natural limit to extension of the joint.

* * * * *